(12) United States Patent
Braun

(10) Patent No.: US 10,537,116 B2
(45) Date of Patent: Jan. 21, 2020

(54) FLAVOUR MODULATION BY BIO-PROCESSING USING CREAM-FLAVOUR FORMING BACTERIA STRAINS

(71) Applicant: NESTEC S.A., Vevey (CH)

(72) Inventor: Marcel Braun, Konolfingen (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 15/640,665

(22) Filed: Jul. 3, 2017

(65) Prior Publication Data
US 2017/0295810 A1    Oct. 19, 2017

Related U.S. Application Data

(62) Division of application No. 13/995,431, filed as application No. PCT/EP2011/073490 on Dec. 20, 2011, now abandoned.

(30) Foreign Application Priority Data

Dec. 20, 2010   (EP) .................................... 10195848

(51) Int. Cl.
| | | |
|---|---|---|
| *A23C 9/123* | (2006.01) | |
| *C12N 1/20* | (2006.01) | |
| *C12P 7/26* | (2006.01) | |
| *C12R 1/46* | (2006.01) | |
| *A23L 27/24* | (2016.01) | |

(52) U.S. Cl.
CPC ............ *A23C 9/1234* (2013.01); *A23L 27/25* (2016.08); *C12N 1/20* (2013.01); *C12P 7/26* (2013.01); *C12R 1/46* (2013.01); *A23Y 2220/31* (2013.01)

(58) Field of Classification Search
None
See application file for complete search history.

(56) References Cited

U.S. PATENT DOCUMENTS

| | | |
|---|---|---|
| 4,889,736 A | 12/1989 | Doornbos et al. |
| 2005/0255193 A1 | 11/2005 | Kuma et al. |
| 2006/0246178 A1 | 11/2006 | Draaisma et al. |
| 2011/0236529 A1* | 9/2011 | Miwa ................... A23C 9/1216 426/36 |

FOREIGN PATENT DOCUMENTS

| | | |
|---|---|---|
| WO | 9933351 | 7/1999 |
| WO | 2008049581 | 5/2008 |

OTHER PUBLICATIONS

Hugenholtz et al. "Diacetyl production by different strains of *Lactococcus lactis* subsp. *lactis* var. *diacetylactis* and *Leuconostoc* spp.," Applied microbiology and biotechnology 38.1 (1992), pp. 17-22. XP000606685.

Boumerdassi et al. "Effect of Citrate on Production of Diacetyl and Acetoin by *Lactococcus lactis* ssp. *lactis* CNRZ 483 Cultivated in the Presence of Oxygen," Journal of dairy science 80.4 (1997), pp. 634-639. XP027047845.

Mutukumira et al. "Characterisation of a malty-compound producing *Lactococcus lactis* subsp. *lactis* biovar. *diacetylactis* C1 strain isolated from naturally fermented milk," Milchwissenschaft 64.1 (2009), pp. 26-29. XP009147172.

Mattheis et al. "Preharvest factors influencing flvaor of fresh fruit and vegetables" 1999 Postharvest Biology and Technology pages vol. 15 227-232.

Wang et al "Study on flavor compounds in milk fermented by *Lactoccocus lactis* ssp. *Lactis* biovar *diacetylactics*" Journal of Northwest A & F University (Nat. Sci. Ed.) vol. 37, No. 4, Apr. 2009, pp. 179-183.

\* cited by examiner

*Primary Examiner* — Felicia C Turner
(74) *Attorney, Agent, or Firm* — K&L Gates LLP

(57) ABSTRACT

A fermentation of a milk source with *Lactococcus lactis* subsp. *lactis diacetylactis* (CNCM No. I-4404) or a *Lactococcus lactis* subsp. *lactis diacetylactis* (CNCM No. I-4405) to form a fermented milk product. The fermented milk product has at least a cream flavour and aroma. The fermented milk product can be in the form of a powder or a concentrate. The fermented milk product has applications in the food industry. A use of a lactic acid bacterium, *Lactococcus lactis* subsp. *lactis diacetylactis* (CNCM No. I-4404) or a *Lactococcus lactis* subsp. *lactis diacetylactis* (CNCM No. I-4405) for the manufacture of butter-cream flavouring milk ingredients containing at least one of diacetyl, acetoin and 3,4-dihydroxy-3,4-dimethyl-2,5-hexanedione.

10 Claims, No Drawings

FLAVOUR MODULATION BY BIO-PROCESSING USING CREAM-FLAVOUR FORMING BACTERIA STRAINS

PRIORITY CLAIM

This application is a divisional of U.S. application Ser. No. 13/995,431 filed Jun. 18, 2013, which is a National Stage of International Application No. PCT/EP11/73490 filed Dec. 20, 2011, which claims priority to European Patent Application No. 10195848.6 filed Dec. 20, 2010, the entire contents of which are incorporated herein by reference.

FIELD OF INVENTION

The present invention relates to the generation of flavour and aroma in milk-based products. The generation of flavour and aroma in milk-based products is achieved using bacteria strains during fermentation of a milk source.

BACKGROUND

Fermentation is a conversion of carbohydrates to organic acids or other compounds using bacteria strains.

Fermented milk products are major consumer products. Fermented milk products can be, for example, cheeses, buttermilks and yoghurts. Fermented milk products are manufactured by fermenting a milk source.

A milk source, for example milk, contains the carbohydrate lactose. During fermentation of the milk source the bacteria strains ferment the carbohydrate lactose to produce lactic acid. The production of lactic acid results in an acidification of the milk source during the manufacture of the fermented milk product. During fermentation of the milk source, other reactions may occur between other substances present in the milk source and the bacterial strains.

A fermentation of the milk source with bacteria strains is responsible for a generation of a flavour and aroma in the fermented milk products. Furthermore the fermentation of the milk source with the bacteria strains increases a shelf-life of the fermented milk products.

The bacteria strains used to ferment the milk source can be lactic acid bacteria strains. The lactic acid bacteria strains include *Lactobacillus, Leuconostoc, Pediococcus, Lactococcus* and *Streptococcus*; as well as the more peripheral *Aerococcus, Carnobacterium, Enterococcus, Oenococcus, Sporolactobacillus, Teragenococcus, Vagococcus* and *Weisella*; these lactic acid bacteria strains belong to the order Lactobacillales.

An international patent application publication No. WO 2008/049581 by the Applicant Nestec SA is titled "Taste and flavour modulation by biotransformation in milk products". The international patent application publication No. WO 2008/049581 discloses a method to promote a non-savoury flavour in a food product.

An international patent application publication No. WO 02/085131 by the Applicant New Zealand Dairy Board is titled "Method of preparing savoury-flavoured products by fermentation of proteins". The international patent application publication No. WO 02/085131 discloses a method for the manufacture of a savoury flavoured product from a source of protein using a combination of two distinct strains of bacteria. The source of protein may be a plant soy, wheat, rice, milk or whey. A first strain of bacteria is selected from the group *Macrococcus, Micrococcus, Entercoccus, Staphylococcus, Brevibacterium, Anthrobacter* and *Corynebacterium*, preferably *Macrococcus caseolyticus*. A second strain of bacteria is selected from the lactic acid bacteria—*Lactococcus, Lactobacillus, Pediococcus* or *Leuconostoc*. The savoury flavoured product may be combined with other ingredients to form products such as cheese, protein-water gels, yoghurts, creams, custards, sauces and confectionary products.

An international patent application publication No. WO 02/00845 by the Applicant Nizo Food Research is titled "Enhanced flavour production in or relating to food by cultivation of various food grade micro-organisms". The international patent application publication No. WO 02/00845 discloses new mixed cultures of two or more micro-organism strains wherein at least one of the micro-organism strains which are comprised in said mixed culture is individually selected on the basis of its ability to perform part of an enzymatic pathway, and said two or more selected micro-organism strains together form a complete pathway towards a desired flavour component. The mixed culture is a culture for the production of a fermented product, such as yogurt or cheese or sausage. Said two or more micro-organism strains are preferably co-cultivated. Particular and preferred embodiments are starter cultures for the manufacture of cheese. The mixed culture comprising a combination of various *Lactoccocus* strains and a combination of a *Brevibacterium* strain and a *Staphylococcus* strain, respectively.

An article by Monnet et al. in a Journal of Microbiological Methods 37 (1999) pp 183-185 is titled "An improved method for screening alpha-acetolactate producing mutants". The article by Monnet et al. discloses that a bacterial strain *Lactococcus Lactis* ssp. *Lactis* Biovar. *Diacetylactis* is used in the dairy industry to produce diacetyl. Diacetyl is a major flavour compound in cultured dairy products.

An article by Boumerdassi et al. in a Journal of Dairy Science Vol. 80 Issue 4 (1997) pp 634-639 is titled "Effect of citrate on production of diacetyl and acetoin by *Lactococcus Lactis* ssp. *Lactis* CNRZ 483 cultivated in the presence of oxygen". The article by Monnet et al. discloses the effects of trisodium citrate addition on growth and formation of diacetyl and acetoin by *Lactococcus Lactis* ssp. *Lactis* CNRZ 483 in a whey based medium.

The article "Characterisation of a malty-compound producing *Lactococcus Lactis* subsp. *Lactis* biovar. *diacetylactis* C1 strain isolated from naturally fermented milk" by Mutukumira et al. (2009) Milchwissenschaft 64(1) pp. 26-29, relates to a strain that produced acceptable fermented milk to a sensory panel despite the presence of a slight malty flavour.

The article "Diacetyl production by different strains of *Lactococcus lactis* subsp. *Lactis* biovar. *diacetylactis* and *Leuconostoc* spp." by Hugenholtz and Starrenburg (1992) Appl. Microbiol. Biotechnol 38, pp. 17-22, relates to the comparison of several strains for product formation from citrate in milk cultures.

However, due to a number of the lactic acid bacteria strains and their interactions with individuals, a selection of certain lactic acid bacteria strains to produce certain flavours and aromas in the fermented milk products is not predictable.

Fermented milk products have a wide variety of flavours and aromas depending upon the milk source and the lactic acid bacteria strains used to ferment the milk source.

There is a need to provide methods and lactic acid bacteria strains that are responsible for specific flavours and aromas in the fermented milk products.

Furthermore, artificial additives are negatively perceived by the consumer. There a need to provide flavour and aromas in a natural way that avoids artificial additives.

There is also a need to provide flavour and aromas which can be used in a wide range of foods.

There is thus a need to overcome the aforementioned problems in the art.

SUMMARY

In a first aspect the present invention relates to a lactic acid bacterium, *Lactococcus lactis* subsp. *lactis diacetylactis* (CNCM No. 1-4404). The present invention also relates to a lactic acid bacterium *Lactococcus lactis* subsp. *lactis diacetylactis* (CNCM No. I-4405).

In a further aspect the present invention relates to a method for the manufacture of a fermented milk product. The fermented milk product has at least a cream flavour and aroma. The method comprises providing a milk source, optionally adding citrate to the milk source to form a supplemented milk source, adding to the milk or supplemented milk source a *Lactococcus lactis* subsp. *lactis diacetylactis* (CNCM No. 1-4404) or a *Lactococcus lactis* subsp. *lactis diacetylactis* (CNCM No. 1-4405) to form a mixture. The mixture is then fermented to manufacture the fermented milk product.

In a further aspect the present invention relates to a fermented milk product with at least a cream flavour and aroma obtainable by the aforementioned method.

In a further aspect the present invention relates to a product for consumption by a mammal comprising a fermented milk product with at least a cream flavour and aroma.

In a further aspect the present invention relates to a food product comprising a lactic acid bacterium, *Lactococcus lactis* subsp. *lactis diacetylactis* (CNCM No. 1-4 4 04) or a *Lactococcus lactis* subsp. *lactis diacetylactis* (CNCM No. 1-4405) and at least one of diacetyl, acetoin and 4-dihydroxy-3,4-dimethyl-2,5-hexanedione.

In a further aspect the present invention relates to a culture comprising lactic acid bacterium, *Lactococcus lactis* subsp. *lactis diacetylactis* (CNCM No. I-4404) or a *Lactococcus lactis* subsp. *lactis diacetylactis* (CNCM No. I-4405).

In a further aspect the present invention relates to a use of a lactic acid bacterium, *Lactococcus lactis* subsp. *lactis diacetylactis* (CNCM No. 1-4404) or a *Lactococcus lactis* subsp. *lactis diacetylactis* (CNCM No. I-4405) to impart at least a cream flavour and aroma to a milk source.

In a further aspect the present invention relates to a use of a lactic acid bacterium, *Lactococcus lactis* subsp. *lactis diacetylactis* (CNCM No. 1-4404) or a *Lactococcus lactis* subsp. *lactis diacetylactis* (CNCM No. 1-4405) for the manufacture of 3,4-dihydroxy-3,4-dimethyl-2,5-hexanedione.

The present inventors were surprised to find that a lactic acid bacterium, *Lactococcus lactis* subsp. *lactis diacetylactis* (CNCM No. 1-4404) or *Lactococcus lactis* subsp. *lactis diacetylactis* (CNCM No. 1-4405) imparts such flavour and aroma to the fermented milk products.

DETAILED DESCRIPTION

For a complete understanding of the present invention and the advantages thereof, reference is made to the following detailed description of the invention.

It should be appreciated that various aspects of the present invention are merely illustrative of the specific ways to make and use the present invention.

The various aspects of the present invention can be combined with other aspects of the present invention and do not limit the scope of the invention when taken into consideration with the claims and the following detailed description.

The present invention concerns fermented milk products. The fermented milk products are manufactured by a fermentation of a milk source with a lactic acid bacterium to provide flavour and aroma to the fermented milk products.

The lactic acid bacterium is a *Lactococcus lactis* subsp. *lactis diacetylactis* (CNCM No. 1-4404) or a *Lactococcus lactis* subsp. *lactis diacetylactis* (CNCM No. 1-4405). The lactic acid bacterium, *Lactococcus lactis* subsp. *lactis diacetylactis* (CNCM No. 1-4404) and the *Lactococcus lactis* subsp. *lactis diacetylactis* (CNCM No. 1-4405) were deposited on 25 Nov. 2010 with the Institut Pasteur—Collection Nationale de Cultures de Mico-organisme (CNCM).

The milk source can be any type of milk, such as cow milk, sheep milk, goat milk and buffalo milk or any mixtures thereof. The milk source may be UHT-treated milk, pasteurised milk or non-pasteurised milk. The milk source may be full fat milk, a skimmed milk or semi-skimmed milk. Furthermore the milk source may be a fresh milk, recombined milk and milk containing vegetable fat and any mixtures thereof.

A conversion of citrate into volatile flavour and aroma compounds plays an important role in food technology. The conversion of citrate into volatile flavour and aroma compounds can be achieved by the lactic acid bacterium. Many milk ingredients contain citrate; however to increase formation it can be desired to supplement the milk source with citrate.

The citrate is converted into volatile flavour and aroma compounds during fermentation. The volatile flavour and aroma compounds have at least a cream like flavour and aroma as discussed below.

The citrate compound e.g. trisodium citrate is added to the milk source in an amount of 0.01 to 5 wt. %, preferably 0.01-2 wt. %, more preferably in an amount of 0.03-1.0 wt. %, most preferably 0.05-0.3 wt. %.

To the supplemented milk source is added the lactic acid bacterium, *Lactococcus lactis* subsp. *lactis diacetylactis* (CNCM No. 1-4404) or the *Lactococcus lactis* subsp. *lactis diacetylactis* (CNCM No. 1-4405).

Lipase can also be added to the milk source or the mixture to produce an enhanced flavour and aroma in the fermented milk products. Lipase hydrolyses fats in the milk source to form for example di-glycerides, monoglycerides and free fatty acids or any mixtures thereof. The di-glycerides, monoglycerides and free fatty acids impart a cream-like flavour to the fermented milk product. Therefore the use of lipase enhances the cream like flavour in the fermented milk product.

Lactase can also be added to the milk source or the mixture to produce desired flavour and aroma in the fermented milk products. Lactase hydrolyses the disaccharide lactose in the milk source into galactose and glucose. Glucose and galactose are used as flavour precursors for caramel-like and sweetened condensed milk-like flavour formation.

If the milk source is non-pasteurised, the milk source or the supplemented milk source may be pasteurised, subjected to ultra-high temperature treatment (UHT-milk) or sterilised under conditions known in the art. The pasteurisation, ultra-high temperature treatment and sterilisation is carried out in a temperature range of 70° C. to 150° C. for a time of between 2 s to 20 min. Alternatively, the milk source may be heat-treated prior to being the supplemented milk source.

The mixture of the supplemented milk source and the lactic acid bacterium (*Lactococcus lactis* subsp. *lactis* biovar *diacetylactis*) is then fermented to manufacture the fermented milk product with the creamy flavour and aroma. The fermentation is allowed to take place for between 6 and 24 hours at a temperature of approximately 30° C.

Optionally, fermentation improving cofactors such as alpha-ketoglutarate, manganese or magnesium salts may also be added prior to the fermentation.

Depending upon the milk source it is to be appreciated that the fermented milk product with a creamy flavour and aroma can be in the form of slurry (yogurt like) or a liquid. The fermented milk product can be dried or concentrated.

The fermented milk product with the creamy flavour and aroma can be dried, preferably by spray-drying and then converted into a powder.

The fermented milk product with the creamy flavour and aroma can have applications in food products and during a manufacture of food products. For example, the powder with the creamy flavour and aroma can have applications in the beverage industry to impart the malty flavour and aroma to beverages. For example, the powder with the creamy flavour and aroma can have applications in the food industry to impart the creamy flavour and aroma to foodstuffs.

EXAMPLES

The manufactured fermented milk products were analysed by an electronic nose based on mass spectrometry and gas chromatography coupled to mass spectrometry (GC-MS).

Analysis with electronic nose based on mass spectrometry is a direct analysis method wherein the fermented milk product is placed directly into the ion source without the need for separation procedures and is therefore time-saving. A determination of volatiles from such a resultant mass spectra contains limited information for the identification of aroma components. Unequivocal identification of the single compounds present is not possible without prior separation and selective fragmentation, i.e., GC-MS.

Gas chromatography coupled to mass spectrometry (GC-MS) provides the necessary separation and detection of volatiles. GC-MS is used for obtaining MS fragments belonging to a specific aroma component. The unambiguous identification of the molecules by GC-MS in combination with olfactometry analysis is mandatory for analysing volatiles with a specific odour.

Commonly used extraction methods for the isolation of volatiles from fermented milk products are vacuum distillation followed by solvent extraction, purge and trap (PT) and headspace techniques such as headspace solid-phase micro extraction (HS-SPME). The purge and trap (PT) and headspace techniques methods identify volatiles with different yield performances, but with comparable reproducibility. PT appeared to be a more sensitive whereas SPME is a more rapid and less expensive technique.

The reagents where used, were used as received without prior treatment unless otherwise stated.

Example 1

A—Reactivation of Lactic Acid Bacterium

The *Lactococcus lactis* subsp. *lactis diacetylactis* (CNCM No. 1-4404) in ampoules was reactivated with 1 ml reconstituted milk under sterile conditions, transferred into sterile glass tubes containing 9 ml reconstituted milk and incubated aerobically at 30° C. for 24 h in the dark.

The bacteria were then stored at 6° C. for two weeks and subsequently inoculated at 0.5% ((v/v) 0.05/10 ml medium) in a culture.

The culture was M17x (M17 Terzaghi Bouillon, Merck 1.15029 and 5 g/l glucose (Merck 8342). After the growth phase (3 days) the flasks were stored at 6° C. to form the reactivated lactic acid bacterium.

Alternatively the culture can be skimmed milk.

B—Milk Source Supplementation with Trisodium Citrate

A 100 mM trisodium citrate solution in water was manufactured. The trisodium citrate solution was filtrated through a pore size of 0.45 µm (Schleicher & Schuell, Whatmann, FP 30/0.45 µm, 7 bar max. CA-S). 500 µl of the trisodium citrate solution was added to 4.5 ml UHT-milk (dilution 1:10) to obtain a supplemented milk source with a final concentration of 10 mM in 5.0 ml.

C—Fermentation

Fermentation in UHT-milk was performed by two approaches (I-II).

I: Index (Inside needle dynamic extraction; Hamilton) headspace sampling of volatile compound fragments in non-supplemented UHT-milk.

II: Tenax (accumulation adsorbens, Marin-Epagnier, Switzerland) headspace sampling of volatile compounds in supplemented milk source UHT-milk (10 mM trisodium citrate).

An aliquot of 50 µl of the reactivated lactic acid bacterium was transferred in 5 ml supplemented milk source UHT milk (1% inoculation) under sterile conditions and incubated at 30° C. aerobically for 16-24 hours in the dark.

An addition of 2.8 g NaCl into the headspace vials helped to expel the volatiles from the fermented milk product into the headspace to get more intense release of the volatiles.

An electronic nose detected the volatile compound fragments at a range of m/z 40-100 for the experiment with non-supplemented UHT-milk (i.e. no trisodium citrate) and at m/z 10-160 for the experiment with supplemented UHT-milk (i.e. with trisodium citrate).

Principle component analysis (PCA) was calculated using the software program "The Unscrambler" (version 9.7). The results were calculated with logarithmised raw data and exclusion of the water and milk blanks. The calculations were done with all variables (MS fragments) included to group the strains in relation to similar MS-fragment patterns and abundance of compounds.

D—Electronic Nose Measurements

Analysis of the fermented milk product by the electronic nose measurements in supplemented milk source UHT-milk was conducted. II: Tenax headspace measurement with 10 mM trisodium citrate supplemented UHT-milk. GC-MS fragments $[M]^+$ were 27, 29, 43, 45, 60, 70, 86, 87, 88 and 135.

E—pH and Redox Potential

A pH of the fermented milk product was determined to be 2.2 with a redox potential of −10 mV.

F—Sensory Assessment of Fermented Milk Product

After fermentation the glass vials were kept closed until sensory evaluation started. Seven persons attended the sensory assessment of the fermented milk product. The sensory assessment was based on the following attributes, scoring is noted with a X. A blank sample (incubated milk) was given as a reference. In order to test the influence of the trisodium citrate samples were also prepared without the trisodium citrate (addition of sterile water only) and presented to the panel. The results are shown below, wherein an X indicated a sensory perception of the fermented milk product to the panelist.

| | | |
|---|---|---|
| | Buttery | XXXX |
| | Bitter/-almond | XX |
| | Flower-like | X |
| | Bread-like | X |
| | Creamy | XXXX |
| | Caramel | — |
| | Strawberry | — |
| | Fresh Fruity | — |
| | Yeast | X |
| | Honey | X |
| | Yoghurt | — |
| | Cheesy | — |
| | Milky | — |
| | Malty | XX |
| | Almond | XX |
| | Nutty | X |
| | Paper-like | — |
| | Sweet | X |
| | Acidic | X |
| | Salty | — |
| | Vanilla | — |

The results of the sensory assessment of the fermented milk product demonstrate that the fermented milk product has a creamy buttery like flavour and aroma.

Example 2

A—Reactivation of Lactic Acid Bacterium

The *Lactococcus lactis* subsp. *lactis diacetylactis* (CNCM No. 1-4405) in ampoules was reactivated with 1 ml reconstituted milk under sterile conditions, transferred into sterile glass tubes containing 9 ml reconstituted milk and incubated aerobically at 30° C. for 24 h in the dark.

The bacteria were then stored at 6° C. for two weeks and subsequently inoculated at 0.5% ((v/v) 0.05/10 ml medium) in a culture.

The culture was M17x (M17 Terzaghi Bouillon, Merck 1.15029 and 5 g/l glucose (Merck 8342). After the growth phase (3 days) the flasks were stored at 6° C. to form the reactivated lactic acid bacterium.

Alternatively the culture can be skimmed milk.

B—Milk Source Supplementation with Trisodium Citrate

A 100 mM trisodium citrate solution in water was manufactured. The trisodium citrate solution was filtrated through a pore size of 0.45 μm (Schleicher & Schuell, Whatmann, FP 30/0.45 μm, 7 bar max. CA-S). 500 μl of the trisodium citrate solution was added to 4.5 ml UHT-milk (dilution 1:10) to obtain a supplemented milk source with a final concentration of 10 mM in 5.0 ml. To the supplemented milk source was added lipase 100 mM.

C—Fermentation

Fermentation in UHT-milk was performed by two approaches (I-II).

I: Index (Inside needle dynamic extraction; Hamilton) headspace sampling of volatile compound fragments in non-supplemented UHT-milk.

II: Tenax (accumulation adsorbens, Marin-Epagnier, Switzerland) headspace sampling of volatile compounds in supplemented UHT-milk (10 mM L-leucine, L-isoleucine, L-valine and L-phenylalanine).

An aliquot of 50 μl of the reactivated lactic acid bacterium was transferred in 5 ml supplemented milk source UHT milk (1% inoculation) under sterile conditions and incubated at 30° C. aerobically for 22 hours in the dark.

An addition of 2.6 g NaCl into the headspace vials helped to expel the volatiles from the fermented milk product into the headspace to get more intense release of the volatiles.

An electronic nose detected the volatile compound fragments at a range of m/z 40-100 for the experiment with non-supplemented UHT-milk (i.e. no trisodium citrate) and at m/z 10-160 for the experiment with supplemented UHT-milk (i.e. with trisodium citrate).

Principle component analysis (PCA) was calculated using the software program "The Unscrambler" (version 9.7). The results were calculated with logarithmised raw data and exclusion of the water and milk blanks. The calculations were done with all variables (MS fragments) included to group the strains in relation to similar MS-fragment patterns and abundance of compounds.

D—Electronic Nose Measurements

Analysis of the fermented milk product by the electronic nose measurements in supplemented milk source UHT-milk was conducted. II: Tenax headspace measurement with 10 mM trisodium citrate supplemented UHT-milk. GC-MS fragments [M]+ were 43, 55, 71, 77, 60, 88, 89, 99, 114, 120 and 131.

F—Sensory Assessment of Fermented Milk Product

After bacterial fermentation the glass vials were kept close until sensory evaluation started. Ten persons attended the sensory assessment of the fermented milk product. The sensory evaluation was a taste evaluation in order to gain information on the in mouth—effect and taste of the obtained fermented milk products.

In each case the samples were pasteurised (85° C. for 15 min in a water bath) and diluted to 1% in UHT milk (at a temperature 20-25° C.). The results shown below detail the inferences of the panelists.

| Panellist | Blank Incubated UHT-milk | Fermented milk product |
|---|---|---|
| 1 | Slightly milky | Intense creamy, Butter |
| 2 | Milky, UHT-milk Slightly Sour | Sweet/creamy, Buttery |
| 3 | Milky, Slight almond, Bitter | Malty, butter |
| 4 | Milky | Cream like |
| 5 | Milky, Cooked | Intense creamy |
| 6 | Milk powder, Sweet | Creamy, Buttery |
| 7 | Milky, Fatty, Buttery, Sweet | Butterish-cream |
| 8 | — | Malty butter |
| 9 | — | Creamy butter |
| 10 | — | Buttery |

The results of the sensory assessment of fermented milk product demonstrate that the fermented milk product had a predominantly creamy like flavour and aroma.

In order to determine the volatile responsible for the creamy buttery flavour an analysis of the GS mass spectra was made with known flavour compounds. It was found that the mass spectrum of 3,4-dihydroxy-3,4-dimethyl-2,5-hexanedione was identical to the mass spectrum of the volatile responsible for the creamy buttery flavour. Furthermore it was found that the compound 3,4-dihydroxy-3,4-dimethyl-2,5-hexanedione has a butter like flavour (see for example U.S. Pat. No. 4,889,736). Thus it was surprising that the lactic acid bacterium, *Lactococcus lactis* subsp. *lactis diacetylactis* (CNCM No. I-4404) or the *Lactococcus lactis* subsp. *lactis diacetylactis* (CNCM No. I-4405) can be used to manufacture 3,4-dihydroxy-3,4-dimethyl-2,5-hexanedione.

Having thus described the present invention in detail, it is to be understood that the detailed description is not intended to limit the scope of the invention thereof.

What is desired to be protected by letters patent is set forth in the following claims.

The invention is claimed as follows:

1. A method for manufacture of a fermented milk product with at least a cream flavor and aroma, the method comprising:
   providing a milk source;
   adding to the milk source at least one lactic acid bacterium selected from the group consisting of a *Lactococcus lactis* subsp. *lactis diacetylactis* (CNCM No. I-4404) and a *Lactococcus lactis* subsp. *lactis diacetylactis* (CNCM No. I-4405) to form a mixture; and
   fermenting the mixture to manufacture a fermented milk product with at least a cream flavor and aroma, wherein the fermenting of the mixture comprises formation of 3,4-dihydroxy-3,4-dimethyl-2,5-hexanedione by the at least one lactic acid bacterium.

2. The method according to claim 1 comprising concentrating the fermented milk product to form a fermented milk product concentrate.

3. The method according to claim 1 comprising drying the fermented milk product to form a powder.

4. The method according to claim 1, wherein the milk source is selected from the group consisting of full fat milk, skimmed milk, semi-skimmed milk, fresh milk, recombined milk, cream, buttermilk, whey, and milk containing vegetable fat.

5. The method according to claim 1 comprising adding at least one of a lipase enzyme or a lactase enzyme to the milk source.

6. The method according to claim 1 comprising adding a fermentation co-factor to the milk source.

7. The method according to claim 1 comprising adding citrate to the milk source to form a supplemented milk source.

8. The method according to claim 7, wherein the citrate is added to the milk source in an amount of 0.01 to 5 wt. %.

9. The method according to claim 1, wherein the cream flavor is a butter-cream flavor.

10. A method to impart at least a cream flavor and aroma to a milk source, the method comprising:
   adding to a milk source at least one lactic acid bacterium to produce at least a cream flavor and aroma selected from the group consisting of a *Lactococcus lactis* subsp. *lactis diacetylactis* (CNCM No. I-4404) and a *Lactococcus lactis* subsp. *lactis diacetylactis* (CNCM No. I-4405); and
   fermenting the milk source with the at least one lactic acid bacterium, wherein the fermenting comprises formation of 3,4-dihydroxy-3,4-dimethyl-2,5-hexanedione by the at least one lactic acid bacterium.

\* \* \* \* \*